United States Patent [19]

McColl et al.

[11] Patent Number: 5,122,143
[45] Date of Patent: Jun. 16, 1992

[54] METHOD AND APPARATUS FOR EXTRACTING A CEMENT MANTLE FROM A BONE RECESS

[75] Inventors: Milton B. McColl, Los Altos Hills; Frederic H. Moll, San Francisco, both of Calif.

[73] Assignee: Origin Medsystems, Inc., San Mateo, Calif.

[21] Appl. No.: 720,656

[22] Filed: Jun. 25, 1991

Related U.S. Application Data

[63] Continuation-in-part of Ser. No. 510,145, Apr. 17, 1990, Pat. No. 5,078,718.

[51] Int. Cl.⁵ .................... A61F 5/00; A61F 2/32
[52] U.S. Cl. ........................ 606/86; 606/99; 606/100
[58] Field of Search ............... 606/87, 88, 89, 90, 606/94, 99, 100, 104, 86, 93; 52/98, 705

[56] References Cited

U.S. PATENT DOCUMENTS

| | | | |
|---|---|---|---|
| 1,227,627 | 5/1917 | Kennedy | 52/705 |
| 4,100,626 | 7/1978 | White | 606/86 |
| 4,476,861 | 10/1984 | Dimakos | 606/100 |
| 4,501,266 | 2/1985 | McDaniel | 606/88 |
| 4,903,692 | 2/1990 | Reese | 606/104 |
| 4,919,153 | 4/1990 | Chin | 606/93 |
| 4,919,679 | 4/1990 | Averill | 606/100 |
| 4,968,316 | 11/1990 | Hergenroeder | 606/90 |
| 4,993,410 | 2/1991 | Kimsey | 606/100 |
| 5,020,519 | 6/1991 | Hayes | 606/104 |

Primary Examiner—Robert A. Hafer
Assistant Examiner—Michael Brown
Attorney, Agent, or Firm—Limbach & Limbach

[57] ABSTRACT

A method and apparatus for removing a pre-placed prosthetic appliance anchored in place in a bone recess by a cement mantle and conditioning the recess for receipt of a replacement appliance. The preplaced appliance is first pulled from the mantle of hardened cement holding it within the recess, thus leaving a cavity within the mantle. A screw threaded post having nuts threadably engaged therewith at longitudinally spaced locations is then anchored within the cavity with a new mass of cement. Thereafter, the post is threadably disengaged from the nuts, leaving the nuts in place within the new mass of cement. A pulling tool is then successively engaged with the nuts and tensioned to incrementally remove the mantle from the recess.

5 Claims, 2 Drawing Sheets

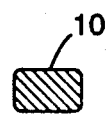
FIG. 4
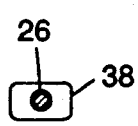
FIG. 5
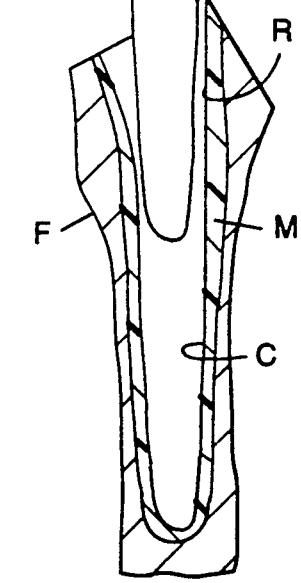
FIG. 1
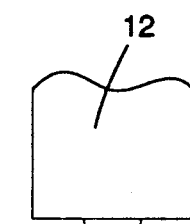
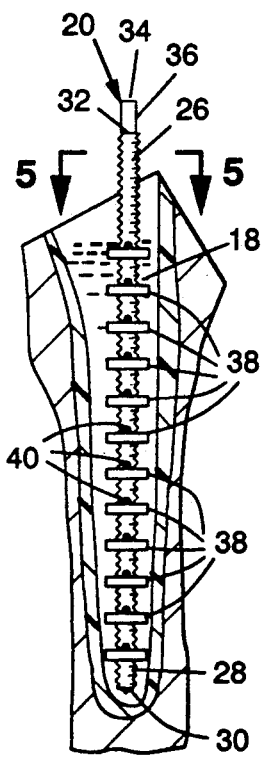
FIG. 2  FIG. 3  FIG. 6

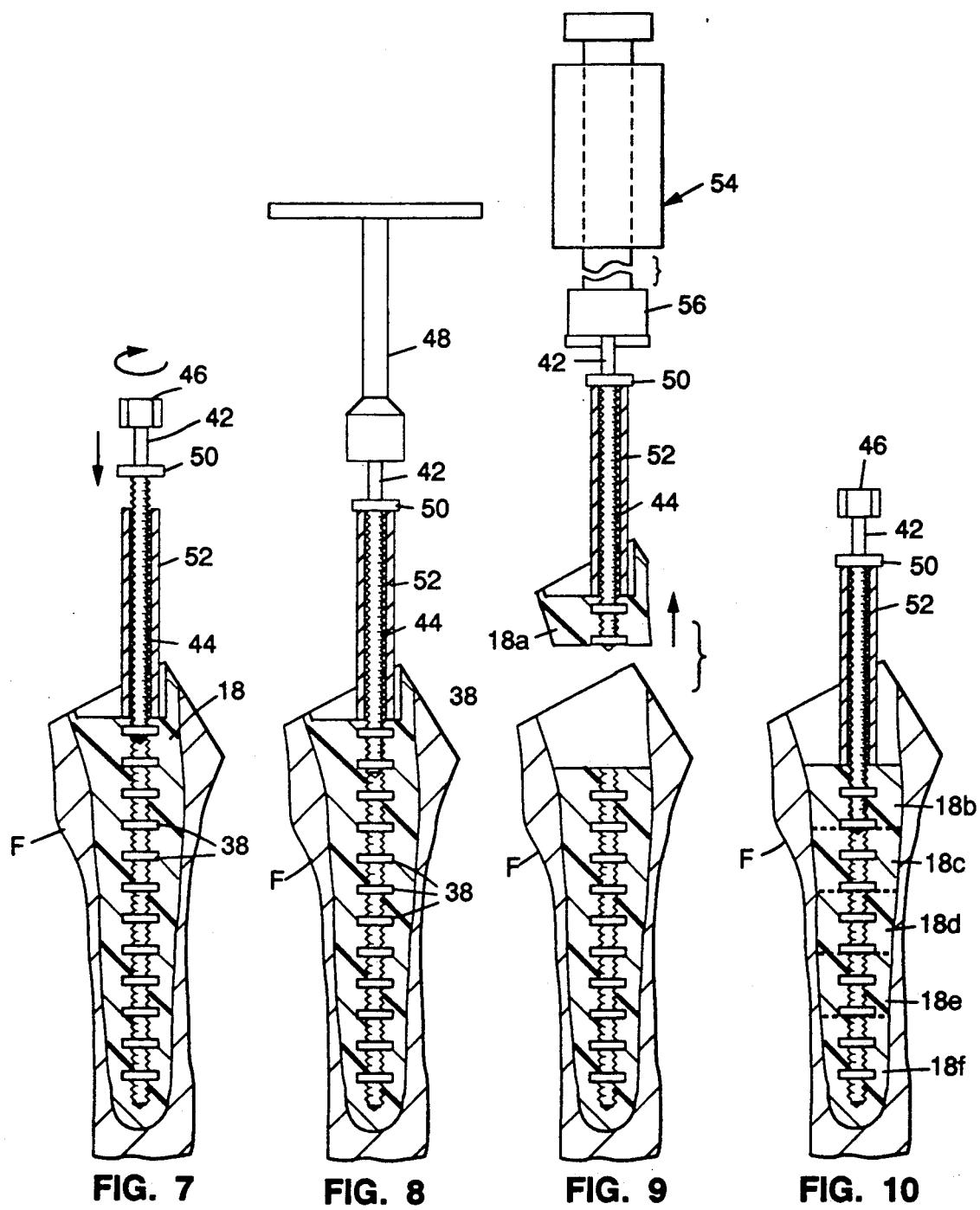

METHOD AND APPARATUS FOR EXTRACTING A CEMENT MANTLE FROM A BONE RECESS

RELATED APPLICATION

This is a continuation-in-part of U.S. patent application Ser. No. 510,145, filed Apr. 17, 1990 and entitled MULTI-PART METHOD AND APPARATUS FOR REMOVING PRE-PLACED PROSTHETIC JOINTS AND PREPARING FOR THEIR REPLACEMENT, now U.S. Pat. No. 5,078,718.

The present invention relates to the replacement of preplaced prosthetic appliances and, more particularly, is concerned with a method and apparatus for extracting the cement mantle used to secure such appliances in place. The invention is especially concerned with an improvement in the cement extraction systems of U.S. Pat. No. 4,919,153, granted Apr. 24, 1990 and U.S. patent application Ser. No. 475,778, filed Feb. 6, 1990.

BACKGROUND OF THE INVENTION

U.S. Pat. No. 4,919,153 teaches a cement extraction system wherein the old cement mantle left after removal of a prosthetic appliance is extracted by injecting new cement into the cavity left in the mantle by removal of the appliance and then engaging a threaded pulling tool with the new cement. In that system, the entire mantle, with the new cement therein, is removed as a unit. The system of U.S. patent application Ser. No. 475,778 is concerned with a variation wherein a die is used to form a screwthreaded passage in the new cement and then pulling tools are successively engaged with segments of the passage to incrementally remove the mantle. This "incremental removal system" has the advantage that the mantle and the bone within which it is received is subjected to reduced stress, as compared to the system of U.S. Pat. No. 4,919,153.

The system of the Ser. No. 475,778 application uses separate extraction rods with a slap hammer to incrementally remove cement segments typically about one inch in length. If the old mantle is very tightly adhered to the bone inside the femoral canal, the force required to extract a segment may exceed the strength of the cement threads. Upon slap hammer use, the extraction rod may eventually pull out of the new cement without an attached cement segment.

Another cause for cement thread strippage with the system of the Ser. No. 475,778 application is the possible malpositioning of the thread forming rod during its placement in the new cement. If the rod is not centered within the cavity in the old mantle, but instead lies against the side of the mantle, insufficient new cement lies between the thread forming rod and the old cement mantle on that side. As a result, incomplete threads may be formed on that side, leading to strippage of the extraction rod from the cement segment upon slap hammer application.

SUMMARY OF THE INVENTION

In the system of the present invention, threaded nuts are received on a thread forming rod of the type used in the system of U.S. patent application Ser. No. 475,778 at approximately one-half inch intervals. The thread forming rod and nut assembly is advanced into the femoral canal after new cement has been injected to fill the canal. The new cement is allowed to polymerize or harden and the thread forming rod is unthreaded and removed from the canal, leaving the nuts embedded in the new cement. An extraction rod is then threaded into the cement threads, as in the system of the Ser. No. 475,778 application. In the present system, however, the threaded channel is reinforced by the metal nuts and strippage of the extraction rod from the cement cannot occur, since the metal extraction rod threads into the metal nuts, as well as the threaded cement channel. In order for the nuts to pull out of the cement segment, an entire column of new cement which is captured by the nut must shear along its interface to the adjacent cement. As a result, all cement above the level of the nut is pulled out during extraction.

A principal object of the present invention is to provide a cement extraction system wherein a threaded channel is formed within the mantle to be removed and reinforced by metal anchors or nuts.

Another object of the invention is to provide such a system wherein the anchors or nuts increase the stress concentration in the cement mantle upon the application of slap hammer force, thus resulting in break-off in a transverse fashion at the level of the nut or anchor.

Still another object of the invention is to provide such a system wherein the anchors or nuts serve to center the thread forming rod in the cavity within the mantle being removed.

Still another object related to the latter object is to provide such a system wherein the new cement within the old cement mantle is evenly distributed around the circumference of the thread forming rod.

Yet another object of the invention is to provide such a system wherein the anchors or nuts may be of varying cross-sectional configuration to accommodate the different cross-sections of various femoral prostheses.

The foregoing and other objects will become more apparent when viewed in light of the following description and accompanying drawings.

BRIEF DESCRIPTION OF THE DRAWINGS

FIG. 1 is a cross-sectional elevational view of the upper femur of a leg, illustrating the step of removing the femoral component of a prosthetic hip joint from a cement mantle within the femur;

FIG. 2 is a cross-sectional elevational view similar to FIG. 1, illustrating the step of filling the cavity within the cement mantle with new cement;

FIG. 3 is a cross-sectional elevational view similar to FIG. 2, illustrating the step of inserting the thread forming rod of the present invention into the new cement within the cavity of the old cement mantle;

FIGS. 4 and 5 are cross-sectional views taken on the planes designated by lines 4—4 and 5—5, respectively, of FIGS. 1 and 3;

FIG. 6 is a cross-sectional elevational view similar to FIG. 3, illustrating the step of removing the thread forming rod from the cured integral mass of cement formed by the old mantle and the newly injected cement;

FIGS. 7 and 8 are cross-sectional elevational views similar to FIG. 6, illustrating an extraction rod being threaded into the threaded passage formed in the mass of cement and engaged with the first two nuts embedded within the mass;

FIG. 9 is a cross-sectional elevational view similar to FIG. 8, illustrating a slap hammer secured to the extraction rod in the process of incrementally removing a first segment of the cement mass from the femoral canal; and, FIG. 10 is a cross-sectional elevational view similar to FIG. 9, illustrating an extraction rod threaded into place within a second segment of the cement mass and engaged with the two nuts embedded within that segment.

DESCRIPTION OF THE PREFERRED EMBODIMENT

The femur shown in FIG. 1 is designated in its entirety by the letter "F" and is shown having a recess "R" formed therein and lined with a cement mantle "M". The mantle "M" was originally used to secure the femoral component 10 of a prosthetic appliance in place within the femur. As shown in FIG. 1, the component is in the process of being removed from the mantle in the direction depicted by the arrow line. Removal of the component 10 leaves a cavity "C" within the mantle "M".

FIG. 2 shows the mantle "M" after the cavity "C" has been cleaned. As there shown, fluid cement is being injected into the cavity "C" from a cartridge 12 having a snout 14 proportioned for extension to the bottom of the cavity. A vent tube 16 also extends to the bottom of the cavity to vent air therefrom and avoid the creation of air pockets within the newly injected cement. The mantle "M" is formed of methylmethacrylate cement and the new cement injected thereinto from the cartridge 12 is of a like composition. Such cement has the quality that the old cement is capable of being partially dissolved and softened by the application of a like new fluid cement thereto. As a result, upon curing, the new cement forms an integral mass with the old cement (see FIG. 6).

FIG. 3 shows the thread forming assembly of the present invention as it is inserted into place within a new mass of fluid methylmethacrylate cement 18 injected into the cavity "C" in the step of FIG. 2. As seen in FIG. 3, the methylmethacrylate cement fills the cavity "C" to approximately the level of the lowermost top extremity of the cavity "C". The thread forming assembly is designated in its entirety by the numeral 20 and comprises: a post 26 having a continuous screw thread 28 formed over the length thereof from its distal end 30 to an upper thread extremity 32 spaced from the proximal end 34 of the post; a square 36 formed on the post 26 between the extremity 32 and the proximal end 34; and, a plurality of nuts 38 threadably received on the post 26 in spaced relationship to one another. In a typical embodiment, the nuts are spaced by approximately one-half inch. Adhesive drops 40 releasably secure the nuts to the post 26 so as to maintain alignment of the nuts and prevent their rotation during placement of the thread forming assembly. Such alignment is important, as the nuts are formed so as to complement the shape of the cavity "C" left by removal of the component 10. A comparison of FIGS. 4 and 5 illustrates this complemental relationship. The adhesive drops 40 also serve to maintain the spaced relationship of the nuts 38.

The adhesive drops are only for temporarily securing the nuts 38 against rotation relative to the post 26. The application of torque to the post functions to break the bond provided by the adhesive drops. This can be seen from FIG. 6 wherein the post is shown after it has been threadably removed from the passage "P" which it formed in the mass 18. As there shown, it will be seen that the passage "P" is formed with an internal screw thread and that the nuts 38 are disposed within the mass 18 at spaced intervals to form part of the threaded passage. The curved arrow line in FIG. 6 depicts the turning of the post 26 to threadably remove the post from the cement mass 18. The straight arrow line in FIG. 6 shows the direction in which the post moves as it is unthreaded.

In the preferred embodiment, both the post 26 and the nuts 38 are fabricated of metal, such as stainless steel. In order to ease removal of the post from the hardened cement mass 18 the post may be coated with a non-stick surface, such as TEFLON (polytetrafluoroethylene). As an alternative to forming the post of metal coated with a non-stick surface, the post may be formed of a plastic material having a low coefficient of friction.

FIG. 7 shows an extraction rod 42 being threaded into the passage "P". The rod 42 has screw threads 44 formed thereon for complemental engagement with the passage "P". A hex head 46 is formed on the upper end of the rod for engagement by a wrench 48 (see FIG. 8). A stop collar or marker 50 is secured to the rod 42 adjacent the hex head 46. A sleeve 52 is slidably received on the rod 42 beneath the collar 50. The sleeve is proportioned for engagement with the top of the cement mass 18 and is of such a length that, upon threaded engagement of the rod 42 with two of the nuts 38 as shown in FIG. 8, the sleeve contacts the collar 50. In use, the surgeon watches the sleeve as the extraction rod is tightened into place and terminates turning of the rod immediately upon engagement of the sleeve with the collar. This limits the degree to which the extraction rod is threaded into place and assures that it will not be over tightened so as to damage the threads within the passage "P".

FIG. 9 shows the extraction rod 42 with a slap hammer 54 secured to its head 46 by a coupling 56. As shown in FIG. 9, the slap hammer has been used to impart upward impact force to the extraction rod and incrementally break away a segment 18a of the cement mass 18. This figure also shows that the cement mass breaks at a plane defined by the lowermost nut in the segment 18a.

FIG. 10 illustrates the segments into which the cement mass 18 is divided for incremental removal. As there shown, the segments are designated 18b, 18c, 18d, 18e and 18f; and the uppermost segment 18b is shown engaged by an extraction rod 42 in a manner corresponding to the extraction rod engagement depicted in FIG. 8. After so engaging the segment 18b, a slap hammer would be secured to the rod 42 to remove the segment 18b in a manner corresponding to that shown in FIG. 9. The remaining segments 18c, 18d, 18e and 18f would be similarly successively engaged and removed. Thus the entire cement mass 18, including the old mantle forming a part thereof, would be incrementally extracted from the recess "R".

Although the illustrated extraction rod 42 is relatively short, it should be understood that longer rods would be used in the removal of the lowermost segments of the cement mass. Other than their length, the structure and mode of operation of such rods, including the stop collars and sleeves thereon, would be identical to that described with reference to the rod 42.

CONCLUSION

From the foregoing description, it is believed apparent that the present invention enables the attainment of the objects initially set forth herein. In particular, the invention provides a system for incrementally removing a cement mantle through means of a threaded passage formed in the mantle, while assuring that the threads within the passage will not be stripped.

We claim:

1. Apparatus for extracting a mantle of cement having a cavity formed therein from a bone recess, said apparatus comprising:
   (a) a post proportioned for extension into the cavity, said post having a longitudinal axis;
   (b) a plurality of anchor elements received around the post and proportioned for receipt therewith in the cavity;
   (c) attaching means releasably securing the anchor elements to the post at longitudinally spaced positions; and,
   (d) pulling means extensible into the anchor elements upon removal of the post therefrom for successive engagement with the anchor elements to impart pulling force thereto.

2. Apparatus according to claim 1 wherein the attaching means comprise complemental screw threads formed on the post and the anchor elements.

3. Apparatus according to claim 2 wherein the pulling means comprises tool having screw threads formed thereon for complemental engagement with the screw threads formed on the anchor elements.

4. Apparatus according to claim 2 further comprising means securing the anchor elements against rotation relative to the post, said means being releasable in response to the application of torque to turn the post about its longitudinal axis relative to the anchor elements.

5. Apparatus according to claim 1 further comprising a non-stick coating on the post.

* * * * *